United States Patent
Goetz et al.

(10) Patent No.: US 10,220,016 B2
(45) Date of Patent: Mar. 5, 2019

(54) METHODS AND MATERIALS FOR ASSESSING CHEMOTHERAPY RESPONSIVENESS AND TREATING CANCER

(71) Applicant: Mayo Foundation for Medical Education and Research, Rochester, MN (US)

(72) Inventors: Matthew P. Goetz, Rochester, MN (US); Judy C. Boughey, Rochester, MN (US); Liewei Wang, Rochester, MN (US); Krishna R. Kalari, Rochester, MN (US); Richard M. Weinshilboum, Rochester, MN (US); Vera J. Suman, St. Charles, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/551,123

(22) PCT Filed: Feb. 17, 2016

(86) PCT No.: PCT/US2016/018282
§ 371 (c)(1),
(2) Date: Aug. 15, 2017

(87) PCT Pub. No.: WO2016/134026
PCT Pub. Date: Aug. 25, 2016

(65) Prior Publication Data
US 2018/0021295 A1    Jan. 25, 2018

Related U.S. Application Data

(60) Provisional application No. 62/118,035, filed on Feb. 19, 2015.

(51) Int. Cl.
*A61K 45/06* (2006.01)
*A61K 31/337* (2006.01)
*C12Q 1/6886* (2018.01)
*G01N 33/574* (2006.01)

(52) U.S. Cl.
CPC .......... *A61K 31/337* (2013.01); *A61K 45/06* (2013.01); *C12Q 1/6886* (2013.01); *G01N 33/57415* (2013.01); *G01N 33/57484* (2013.01); *C12Q 2600/106* (2013.01); *C12Q 2600/136* (2013.01); *C12Q 2600/156* (2013.01); *G01N 2800/52* (2013.01)

(58) Field of Classification Search
CPC .... A61K 31/337; A61K 45/06; C12Q 1/6886; G01N 33/574
See application file for complete search history.

(56) References Cited

U.S. PATENT DOCUMENTS

| | | |
|---|---|---|
| 2008/0214548 A1 | 9/2008 | Flohr et al. |
| 2013/0225436 A1 | 8/2013 | Sidhu et al. |
| 2013/0274127 A1 | 10/2013 | Baker et al. |
| 2014/0206545 A1 | 7/2014 | Baker et al. |

FOREIGN PATENT DOCUMENTS

| | | |
|---|---|---|
| WO | WO 2005/119260 | 12/2005 |
| WO | WO 2007/009715 | 1/2007 |
| WO | WO 2013040433 | * 3/2013 |
| WO | WO 2014/071419 | 5/2014 |

OTHER PUBLICATIONS

Sandford (Kidney International (2009) 75, 765-767) and further in view of Colby et al(US 23009/0299645).*
Kann et al. Bioinformatics 26(19( 2458-2459 (2010)(2).*
Human Protein AtlaS (2017).*
Gout et al. "PKDB: Polycystic Kidney Disease Mulation Dalabase—a gene variant database for autosomal dominant polycystic kidney disease," *Hum Mutation.*, 28:654-659, Mar. 16, 2007.
GenBank Accession No. NC_000016.10, "*Homo sapiens* chromosome 16, GRCh37.p13 Primary Assembly," Aug. 13, 2013, 2 pages.
International Preliminary Report on Patentability in International Application No. PCT/US2016/018282, dated Aug. 31, 2017, 7 pages.
International Search Report and Written Opinion in International Application No. PCT/US2016/018282, dated Jun. 10, 2016, 9 pages.
Rodon et al., "Development of PI3K inhibitors: lessons learned from early clinical trials," Nature Reviews., 10:143-153, Mar. 2013.
Zheng et al., "PKD1 Phosphorylation-Dependent Degradation of SNAIL by SCF-FBXO11 Regulates Epithelial-Mesenchymal Transition and Metastasis," Cancer Cell., 26(3):358-373, Sep. 8, 2014.
Aleo et al., "Identification of new compounds that trigger apoptosome-independent caspase activation and apoptosis," Cancer Res., 66(18):9235-44, Sep. 2006.

(Continued)

*Primary Examiner* — Shirley V Gembeh
(74) *Attorney, Agent, or Firm* — Fish & Richardson P.C.

(57) ABSTRACT

This document provides methods and materials involved in assessing chemotherapy responsiveness and treating cancer (e.g., breast cancer). For example, methods and materials for determining whether or not a cancer patient (e.g., a breast cancer patient) is likely to respond to chemotherapy (e.g., a taxane therapy) based at least in part on the presence of a variant in the mammal's polycystic kidney disease gene 1 (PKD1) are provided. In addition, methods and materials involved in treating mammals having cancer (e.g., breast cancer) by administering an inhibitor of ubiquitin specific peptidase 2 (USP2) polypeptide activity (e.g., NSC-632839, a 2-cyano-pyrimidine, or a 2-cyano-triazine) in combination with another chemotherapeutic agent such as a taxane therapy are provided.

10 Claims, 17 Drawing Sheets

(56) References Cited

OTHER PUBLICATIONS

Borges et al., "A combination treatment with DNA methyltransferase inhibitors and suramin decreases invasiveness of breast cancer cells," Breast Cancer Res. Treat., 144:79-91, Feb. 2014.
European Search Report for European Application No. EP 16752983, dated Sep. 18, 2018, 26 pages.
Housset et al., "[Cystic liver diseases. Genetics and cell biology]," Gastroenterol Clin. Biol., Aug.-Sep. 2005.
Liberati et al., "Oncogenic and anti-oncogenic effects of transient receptor potential channels," Curr. Top Med. Chem., 13(3):344-66, Feb. 2013.
Ma et al., "Identification of genes that modulate sensitivity of U373MG glioblastoma cells to cis-platinum," Anticancer Drugs, 17(7):733-51, Aug. 2006.
Santoni et al., "TRP channels and cancer: new targets for diagnosis and chemotherapy," Endocr Metab Immune Disord Drug Targets., 11:54-67, Mar. 2011.

\* cited by examiner

Molecular Formula: $C_{26}H_{28}ClN_5O_2$   Molecular Weight: 477.98582 g/mol

AGN-PC-00RLLF

Also known as: HMS1836H22, AKOS001867273, NCGC00112838-01, C768-0171, ethyl 1-[6-ethoxy-3-(4-methylbenzoyl)quinolin-4-yl]peperidine-3-carboxylate Molecular Formula: $C_{27}H_{30}N_2O_4$   Molecular Weight: 446.5381 g/mol

AGN-PC-00RCGU

Also known as: MolPort-002-803-152, MolPort-019-766-624, HMS 1842A02, AKOS001510670, AKOS022046292, NCGC00114637-01

Molecular Formula: $C_{30}H_{40}N_2O_4$   Molecular Weight: 492.6496 g/mol

AE-848/42799010

Also known as: HMS1892A05, CCG-83762, NCGC00132282-01, G617-0022

Molecular Formula: $C_{15}H_{18}N_2OS$ Molecular Weight: 274.38122 g/mol

AC1OOKVS

Also know as: AC1O759Z, MolPort-002-811-247, HMS1801J07, N-(3-chloro-2-methylphenyl)-3a, 4, 5, 9b-tetrahydro-3H-cyclopentra[c]quinoline-8-sulfonamide, ZINC08454094, AKOS001663629

Molecular Formula: $C_{26}H_{25}ClN_2O_2S$ Molecular Weight: 465.0069 g/mol

AH487/14404015

Also known as: AGN-PC-0KA5LP, STOCK1S-06342, MolPort-000-515-309, HMS18012O05, STK072327, AKOS000670166

Molecular Formula: $C_{24}H_{31}NO$   Molecular Weight: 349.50904 g/mol

AC1MJC1L

Also known as: ML364, NCGC00262995-01, KB-267455, 2-[(4-methylphenyl)sulfonylamino]-n-(4-phenyl-1,3-thiazol-2-yl)-4-(trifluoromethyl)

Molecular Formula: $C_{24}H_{18}F_3N_3O_3S_2$   Molecular Weight: 517.54323 g/mol

NCGC00262995-02

METHODS AND MATERIALS FOR ASSESSING CHEMOTHERAPY RESPONSIVENESS AND TREATING CANCER

CROSS REFERENCE TO RELATED APPLICATIONS

This application is a National Stage application under 35 U.S.C. § 371 of International Application No. PCT/US2016/018282, having an International Filing Date of Feb. 17, 2016, which claims the benefit of U.S. Provisional Ser. No. 62/118,035, filed Feb. 19, 2015. The disclosure of the prior application is applications are considered part of (and are incorporated by reference in) the disclosure of this application.

BACKGROUND

1. Technical Field

This document relates to methods and materials involved in assessing chemotherapy responsiveness and treating cancer (e.g., breast cancer). For example, this document provides methods and materials for determining whether or not a cancer patient (e.g., a breast cancer patient) is likely to respond to chemotherapy (e.g., a taxane therapy) based at least in part on the presence of a variant in the mammal's polycystic kidney disease gene 1 (PKD1). This document also provides methods and materials involved in treating mammals having cancer (e.g., breast cancer) by administering an inhibitor of ubiquitin specific peptidase 2 (USP2) polypeptide activity (e.g., NSC-632839, a 2-cyano-pyrimidine, or a 2-cyano-triazine) in combination with another chemotherapeutic agent such as a taxane therapy.

2. Background Information

Breast cancer is a cancer that develops from breast tissue and is the most common invasive cancer in women. Breast cancer is usually treated with surgery, which may be followed by chemotherapy or radiation therapy, or both chemotherapy and radiation therapy.

SUMMARY

This document provides methods and materials involved in assessing chemotherapy responsiveness. For example, this document provides methods and materials for determining whether or not a cancer patient (e.g., a breast cancer patient) is likely to respond to chemotherapy (e.g., a taxane therapy) based at least in part on the presence of a variant in the mammal's polycystic kidney disease gene 1 (PKD1). As described herein, cancer patients having at least one variant allele of the PKD1 gene (e.g., the G→A allele; position=chromosome 16:2164211; rs148709380 G/A) can be classified as having cancer responsive to chemotherapy with agents such as taxanes (e.g., paclitaxel or docetacel) or taxanes followed by anthracycline-based chemotherapy.

Having the ability to identify cancer patients that are likely to respond to chemotherapy (e.g., a taxane therapy) can allow doctors and patients to proceed with appropriate treatment options. For example, a patient identified as having at least one variant allele of the PKD1 gene can be treated with a taxane agent (e.g., paclitaxel or docetacel) or a taxane agent followed by anthracycline-based chemotherapy. In some cases, a patient identified as not having at least one variant allele of the PKD1 gene can be treated with carboplatin, a PI3K inhibitor, a USP2 inhibitor, an AKT inhibitor, or an mTOR inhibitor. In some cases, a patient identified as not having at least one variant allele of the PKD1 gene can be treated with a USP2 inhibitor together with a taxane agent (e.g., paclitaxel or docetacel).

This document also provides methods and materials involved in treating a mammal (e.g., a human) having cancer (e.g., breast cancer). For example, this document provides methods and materials for using an inhibitor of USP2 polypeptide activity (e.g., NSC-632839, a 2-cyano-pyrimidine, or a 2-cyano-triazine) in combination with another chemotherapeutic agent such as a taxane therapy to treat cancer (e.g., breast cancer).

In general, one aspect of this document features a method for identifying a mammal having cancer as being likely to respond to chemotherapy. The method comprises, or consists essentially of, (a) detecting, in a sample obtained from the patient, the presence of at least one variant PKD1 allele, and (b) classifying the patient as being likely to respond to the chemotherapy based at least in part on the presence. The mammal can be a human. The cancer can be breast cancer. The variant PKD1 allele can be a G→A allele of rs148709380. The chemotherapy can be a taxane therapy.

In another aspect, this document features a method for treating cancer. The method comprises, or consists essentially of, (a) administering a USP2 inhibitor to a mammal having cancer, and (b) administering a chemotherapeutic agent to the mammal. The mammal can be a human. The cancer can be breast cancer. The mammal can comprise a variant PKD1 allele. The variant PKD1 allele can be a G→A allele of rs148709380. The USP2 inhibitor can be NSC-632839 or a compound set forth in FIGS. 10A-G. The chemotherapeutic agent can be a taxane agent.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
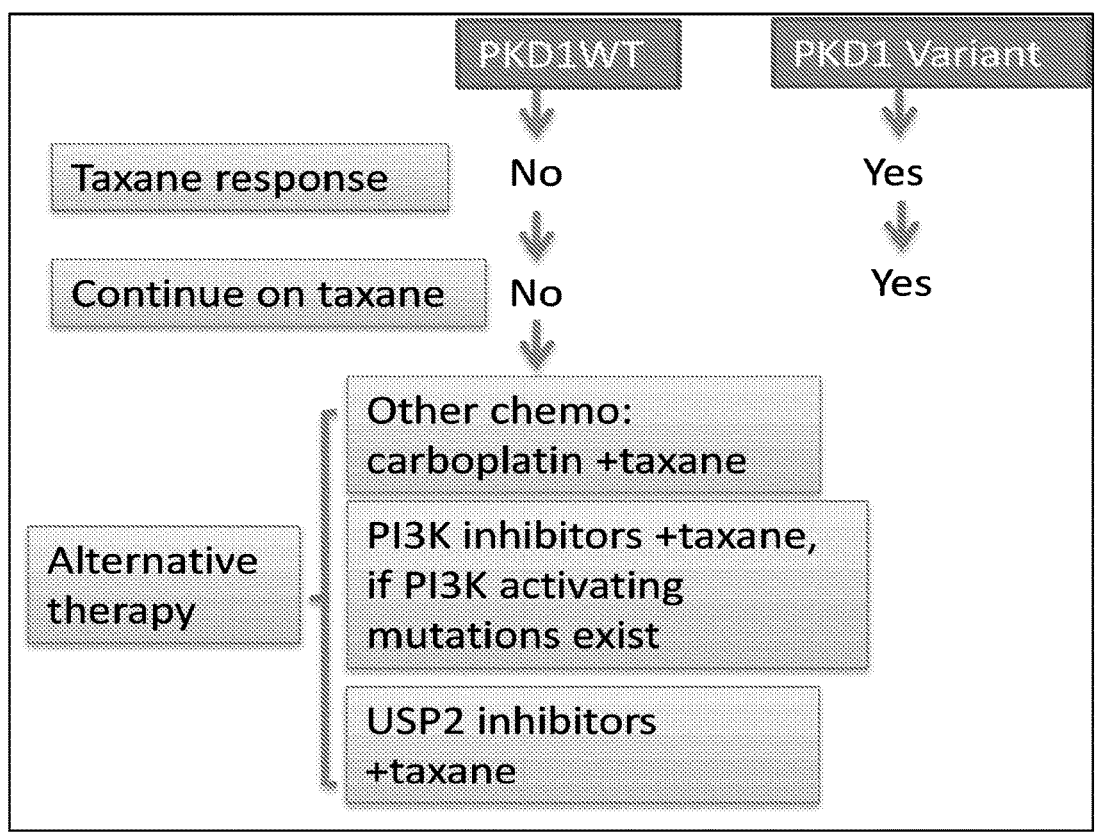
FIG. 1 is a diagram of possible cancer treatments for mammals having cancer with wild-type PKD1 or variant PKD1 genotypes.

This document provides methods and materials for assessing chemotherapy responsiveness. For example, this document provides methods and materials for determining whether or not a mammal having cancer is likely to respond to chemotherapy (e.g., a taxane therapy) based at least in part on the presence of a variant in the mammal's PKD1 gene. Any appropriate mammal can be assessed as described herein. For example, humans, non-human primates, monkeys, horses, bovine species, porcine species, dogs, cats, mice, and rats having cancer can be assessed to determining whether or not the mammal is likely to respond to chemotherapy (e.g., a taxane therapy). In addition, a mammal having any particular type of cancer can be assessed as described herein. For example, mammals with breast cancer, ovarian cancer, lung cancer, Kaposi's sarcoma cancer, or other solid cancers can be assessed to determine whether or not the mammal is likely to respond to chemotherapy (e.g., a taxane therapy).

As described herein, a mammal having a variant in the PKD1 gene can be classified as being likely to respond to chemotherapy such as taxane therapies, anthracycline therapies, and gemcitabine therapies. Examples of taxane therapies include, without limitation, cancer treatments that involve administering taxane agents such as paclitaxel, docetacel, or other microtubule disrupting agents such as vinblastine, vincristine, or vinorelbine. In some cases, drugs used to treat gout or chochicine can be used as a mitotic inhibitor to treat a mammal having cancer with a variant in the PKD1 gene. Examples of anthracycline therapies include, without limitation, cancer treatments that involve administering anthracycline agents such as doxorubicine, daunorubicin, epirubicin, idarubicin, valrubicin, and mitoxantrone. In some cases, a mammal (e.g., a human) having a variant in the PKD1 gene can be classified as being likely to respond to chemotherapy the includes administering a taxane agent (e.g., paclitaxel or docetacel) and an anthracycline agent.

Examples of variants within the PKD1 gene of a mammal that can be used, at least in part, to classify the mammal as being likely to respond to chemotherapy include, without limitation, a variation at location chromosome16:2164211 (see, e.g., GenBank® Accession No. NC_000016.10). For example, a mammal having at least one G→A allele for the rs148709380 polymorphic location can be classified as being likely to respond to chemotherapy.

Any appropriate method can be used to detect the presence or absence of variants within the PKD1 gene of a mammal. For example, sequencing techniques can be used to sequence the PKD 1 alleles present within a sample (e.g., a cancer cell sample or cancer tissue sample) obtained from a mammal having cancer.

This document also provides methods and materials to assist medical or research professionals in determining whether or not a mammal (e.g., a human cancer patient) is likely to respond to chemotherapy. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the presence of one or more variant PKD1 alleles as described herein, and (2) communicating information about those one or more variant PKD1 alleles to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides methods and materials involved in treating mammals having cancer (e.g., breast cancer) by administering an inhibitor of USP2 polypeptide activity (e.g., NSC-632839, a 2-cyano-pyrimidine, or a 2-cyano-triazine) in combination with another chemotherapeutic agent such as a taxane therapy. Any appropriate mammal having cancer can be treated as described herein. For example, humans and other primates such as monkeys having cancer can be treated with an inhibitor of USP2 polypeptide activity in combination with another chemotherapeutic agent such as a taxane therapy. In some cases, dogs, cats, horses, bovine species, porcine species, mice, or rats can be treated with an inhibitor of USP2 polypeptide activity in combination with another chemotherapeutic agent such as a taxane therapy as described herein. In addition, a mammal having any particular type of cancer can be treated as described herein. For example, a mammal with breast cancer, ovarian cancer, lung cancer, Kaposi's sarcoma cancer, or other solid cancers can be treated with an inhibitor of USP2 polypeptide activity in combination with another chemotherapeutic agent such as a taxane therapy as described herein. In some cases, a mammal determined to have cancer containing at least one allele of a variant PKD1 gene can be treated with an inhibitor of USP2 polypeptide activity in combination with another chemotherapeutic agent such as a taxane therapy.

Any appropriate method can be used to identify a mammal having cancer (e.g., breast cancer or breast cancer containing at least one allele of a variant PKD1 gene). For example, imaging, biopsy, pathology, and sequencing techniques can be used to identify a human having breast cancer that includes a variant PKD1 gene.

Once identified as having cancer, the mammal can be administered one or more USP2 inhibitors. Examples of USP2 inhibitors include, without limitation, NSC-632839 (also known as 3,5-Bis[(4-methylphenyl)methylene]-4-piperidone hydrochloride), 2-cyano-pyrimidines, 2-cyano-triazines, and those compounds listed in FIGS. 10A-G. 2-cyano-pyrimidines and 2-cyano-triazines can be obtained as described elsewhere (see, e.g., WO 2007/009715). Examples of chemotherapeutic agents that can be used in combination with a USP2 inhibitor include, without limitation, taxane therapies, anthracycline therapies, and gemcitabine therapies. Examples of taxane therapies include, without limitation, cancer treatments that involve administering taxane agents such as paclitaxel, docetacel, or other microtubule disrupting agents such as vinblastine, vincristine, or vinorelbine. In some cases, drugs used to treat gout or chochicine can be used as described herein to treat a mammal having cancer with a variant in the PKD1 gene. Examples of anthracycline therapies include, without limitation, cancer treatments that involve administering anthracycline agents such as doxorubicine, daunorubicin, epirubicin, idarubicin, valrubicin, or mitoxantrone. In some cases, one or more USP2 inhibitors (e.g., one, two, three, four, five, or more USP2 inhibitors) can be administered to a mammal to increase responsiveness to such chemotherapeutic agents. For example, one or more USP2 inhibitors (e.g., one, two, three, four, five, or more USP2 inhibitors) can be administered to a mammal with breast cancer to increase the responsiveness of the breast cancer to taxane agents such as paclitaxel or docetacel.

In some cases, one or more USP2 inhibitors can be formulated into a pharmaceutically acceptable composition for administration to a mammal having cancer (e.g., breast cancer). For example, a therapeutically effective amount of NSC-632839 or a compound set forth in FIGS. 10A-G can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more USP2 inhibitors can be designed for oral or parenteral (including subcutaneous, intramuscular, intravenous, and intradermal) administration. When being administered orally, a pharmaceutical composition containing one or more USP2 inhibitors can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

Such injection solutions can be in the form, for example, of a sterile injectable aqueous or oleaginous suspension. This suspension may be formulated using, for example, suitable dispersing or wetting agents (such as, for example, Tween 80) and suspending agents. The sterile injectable preparation can be a sterile injectable solution or suspension in a non-toxic parenterally-acceptable diluent or solvent, for example, as a solution in 1,3-butanediol. Examples of acceptable vehicles and solvents that can be used include, without limitation, mannitol, Ringer's solution, and isotonic sodium chloride solution. In addition, sterile, fixed oils can be used as a solvent or suspending medium. In some cases, a bland fixed oil can be used such as synthetic mono- or di-glycerides. Fatty acids, such as oleic acid and its glyceride derivatives can be used in the preparation of injectables, as can natural pharmaceutically-acceptable oils, such as olive oil or castor oil, including those in their polyoxyethylated versions. In some cases, these oil solutions or suspensions can contain a long-chain alcohol diluent or dispersant.

In some cases, a pharmaceutically acceptable composition including one or more USP2 inhibitors can be administered locally or systemically. For example, a composition containing an USP2 inhibitor can be administered locally by injection into lesions at surgery or by subcutaneous administration of a sustained release formulation. In some cases, a composition containing an USP2 inhibitor can be administered systemically orally or by injection to a mammal (e.g., a human).

Effective doses can vary depending on the severity of the cancer, the route of administration, the age and general health condition of the subject, excipient usage, the possibility of co-usage with other therapeutic treatments such as use of chemotherapeutic agents, and the judgment of the treating physician.

An effective amount of a composition containing one or more USP2 inhibitors can be any amount that increases the mammal's responsiveness to chemotherapeutic agent (e.g., a taxane agent) without producing significant toxicity to the mammal. For example, an effective amount of a USP2 inhibitor can be from about 0.01 mg/kg to about 10 mg/kg. In some cases, between about 10 mg and about 1500 mg of a USP2 inhibitor can be administered to an average sized human (e.g., about 70-75 kg human) daily for about one week to about one year (e.g., about two weeks to about four months). If a particular mammal fails to respond to a particular amount, then the amount of USP2 inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that increases the mammal's responsiveness to chemotherapeutic agent (e.g., a taxane agent) without producing significant toxicity to the mammal. For example, the frequency of administration can be from about once a week to about once every two to three weeks. The frequency of administration can remain constant or can be variable during the duration of treatment. A course of treatment with a composition containing one or more USP2 inhibitors can include rest periods. For example, a composition containing one or more USP2 inhibitors can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition containing one or more USP2 inhibitors can be any duration that increases the mammal's responsiveness to chemotherapeutic agent (e.g., a taxane agent) without producing significant toxicity to the mammal. Thus, the effective duration can vary from several days to several weeks, months, or years. In general, the effective duration for the treatment with USP2 to increase the responsiveness to chemotherapeutic agent can range in duration from six months to one year. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and the severity of one or more symptoms related to the cancer being treated (e.g., breast cancer) can be monitored. Any appropriate method can be used to determine whether or not the severity of a symptom is reduced. For example, the severity of a symptom of breast cancer (e.g., cancer recurrence) can be assessed using imagine and pathology assessment of biopsy samples or surgical samples.

The invention will be further described in the following examples, which do not limit the scope of the invention described in the claims.

EXAMPLES

Example 1—Determining Chemotherapy Responsivenes

A prospective neoadjuvant study was developed using breast cancer patients with high risk disease. The patients were treated weekly with paclitaxel followed by anthracycline-based chemotherapy. Percutaneous tumor biopsies were obtained before, during, and after chemotherapy for sequencing analysis. In particular, patients underwent percutaneous tumor biopsy at baseline and after 12 weeks of paclitaxel treatment. Response to paclitaxel at 12 weeks was defined as patients with complete response by imaging (e.g., no mass or distortion identified on ultrasound). All other patients underwent repeat biopsy, and response was defined as histologic absence of invasive breast cancer. Those with histologic residual invasive disease with KI67<15% were classified as responders. Patients with histologic residual invasive disease with KI67≥15% were classified as non-responders. Exome sequencing was performed on tissue from percutaneous tumor biopsies and also on blood DNA. RNA sequencing was performed on tissue from the percutaneous tumor biopsies. Additionally, patient derived xenografts were established in mice from tissue obtained from percutaneous tumor biopsy samples at time of initial diagnosis. Non-SCID mice and NSG mice (estrogen supplemented) were implanted within 30 minutes of biopsy with tumor samples.

Of the first 44 patients that completed paclitaxel therapy, 18 patients exhibited either a Triple Negative or Luminal B clinical subtype breast cancer. 9 patients were classified as responders, and 9 patients were non-responders to paclitaxel according to KI-67 levels.

A single nucleotide variant was identified by RNA sequencing (PKD1 16_2164211_G_A; G→A allele of rs148709380). This variant was associated with a response to paclitaxel treatment. Specifically, all non-responders had evidence for the PKD1 wild type alleles (G/G genotype), and all responders had one PKD 1 variant allele (G/A genotype) (Table 1).

TABLE 1

| Clinical Characteristics | Overall | Responders: 12 week Ki-67 <15% (n = 9) | Non-Responders: 12 week Ki-67 ≥15% (n = 9) |
|---|---|---|---|
| Median Age | 49 | 53 | 45 |
| T stage T2/T3 | 14 (78%) | 7 (78%) | 7 (78%) |
| Node Positive | 8 (44%) | 4 (44%) | 4 (44%) |
| Triple negative | 10 (56%) | 6 (67%) | 4 (44%) |
| Luminal B | 8 (44%) | 3 (33%) | 5 (56%) |
| Ki-67 after 12 Weeks of T | | Median 5% (0-11%) | Median 35% (17-60%) |
| PKD1 16_2164211_G_A | | 9 (100%) | 0 (0%) |
| 16_2164211_G_G | | 0 (0%) | 9 (100%) |

Figure 2:
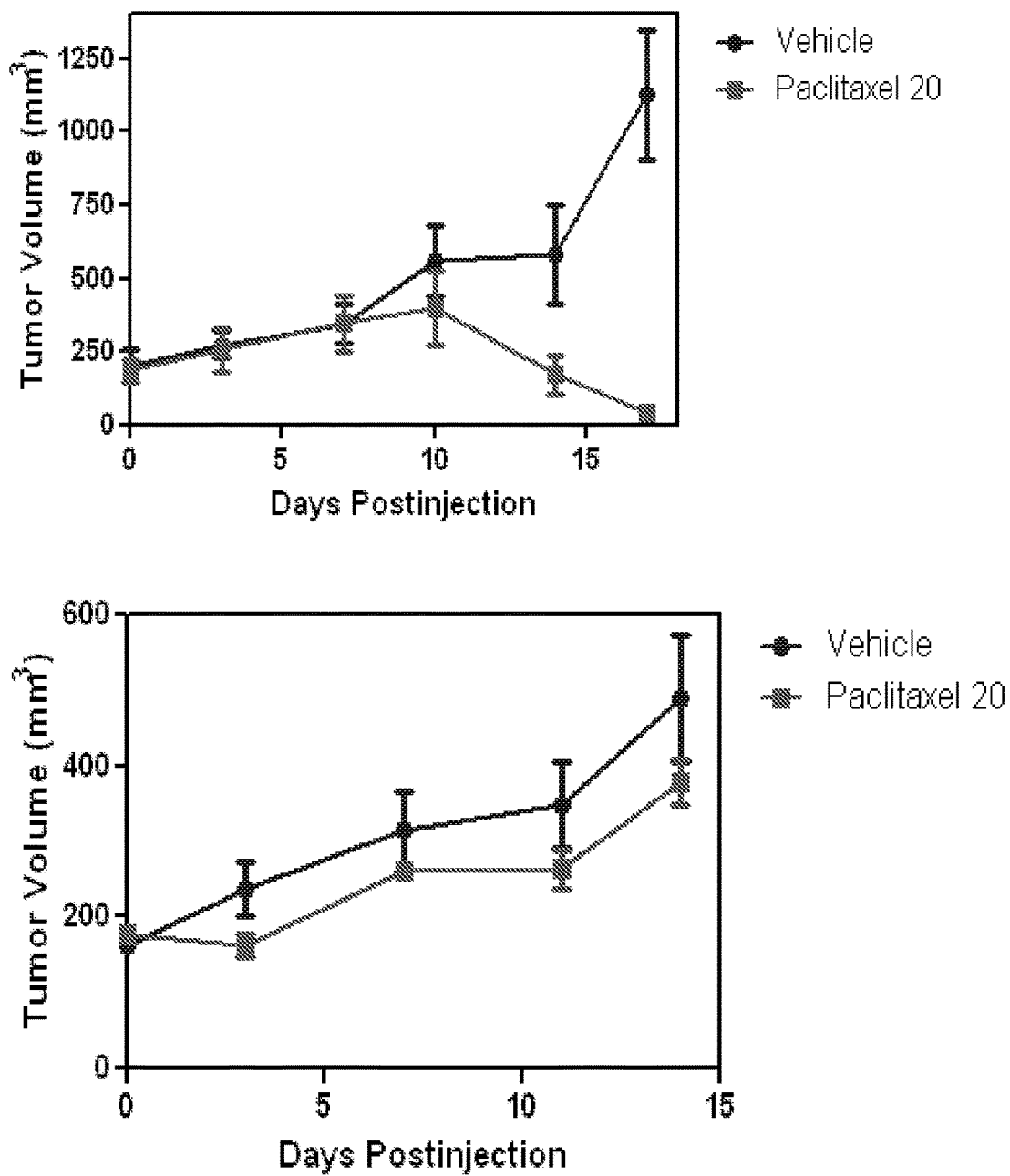
FIG. 2. Mice with tumors derived from two individual patients with WT (A) and variant (B) PKD1 rs148709380 were treated with paclitaxel 20 mg/kg (ip) every three days. Tumor sizes were measured at indicated days after starting the drug.

Xenografts were generated from two patients with the PKD1 wild type alleles (G/G) and from two patients with the PKD 1 variant allele genotype (G/A). From these xenografts, markedly different levels of AKT, pAKT (s308) PI3K p110, pPDK1, pPTEN, pGSK3b, and pmTOR were observed. Specifically, xenografts from patients with the variant allele exhibited markedly reduced levels of these polypeptides as compared to xenografts from patients with the wild type allele. When examining the response to paclitaxel in vivo, significantly greater growth inhibition was observed with xenografts from the PKD1 variant patients as compared to that observed with xenografts from wild type PKD1 patients (FIG. 2).

Figure 3:
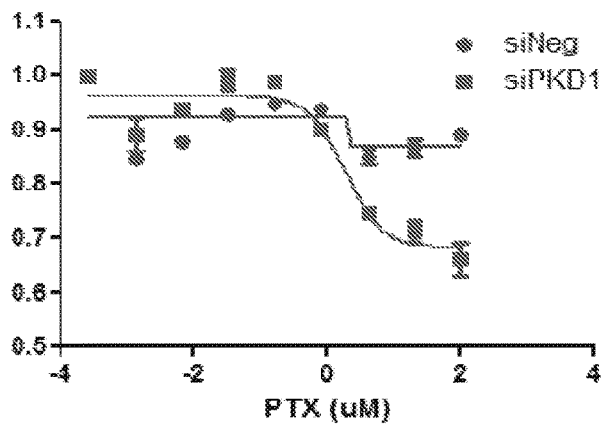
FIG. 3. Down regulation of PKD1 sensitize multiple breast cancer cells to taxane.
Figure 3:
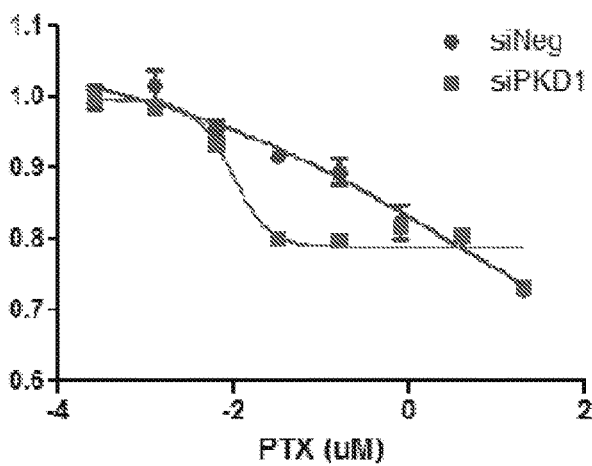
Figure 3:
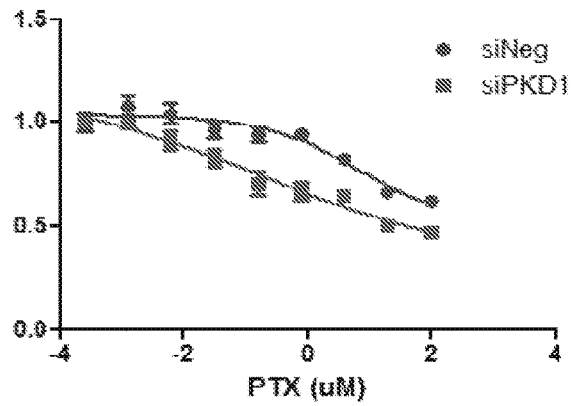
Figure 4:
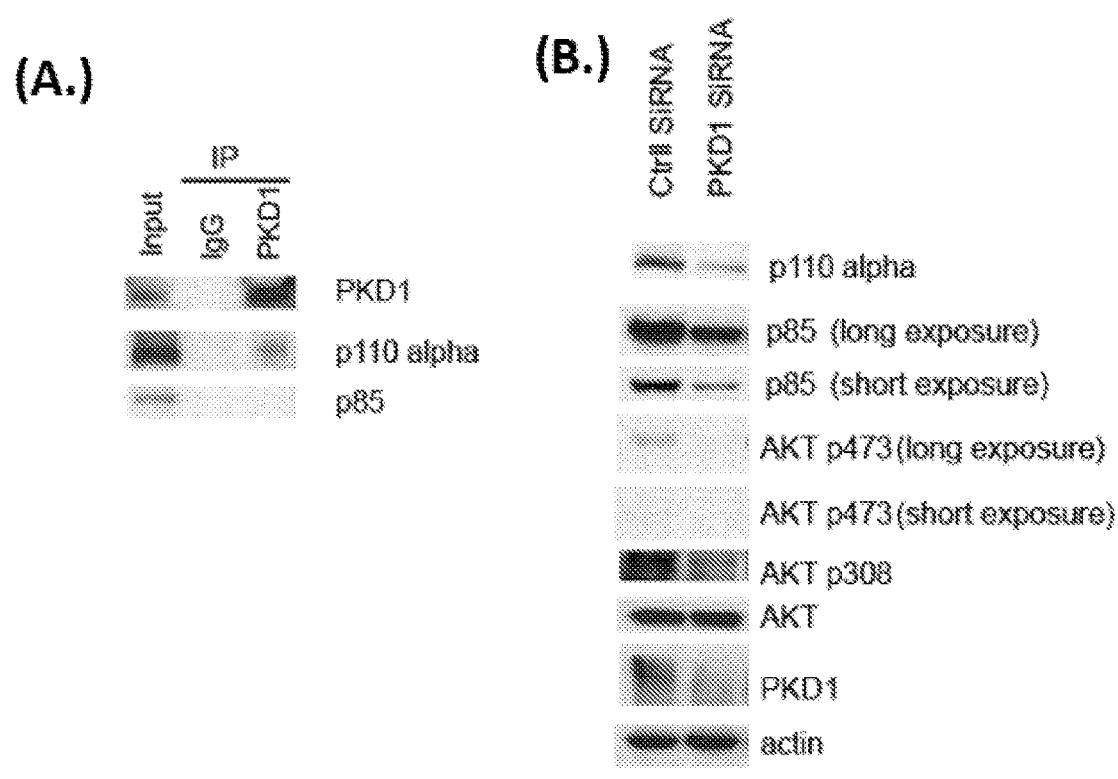
FIGS. 4A-B. Downregulation of PKD1 destabilized P110α and p85 and downstream AKT activity (pAKT308 and 473).
Figure 5:
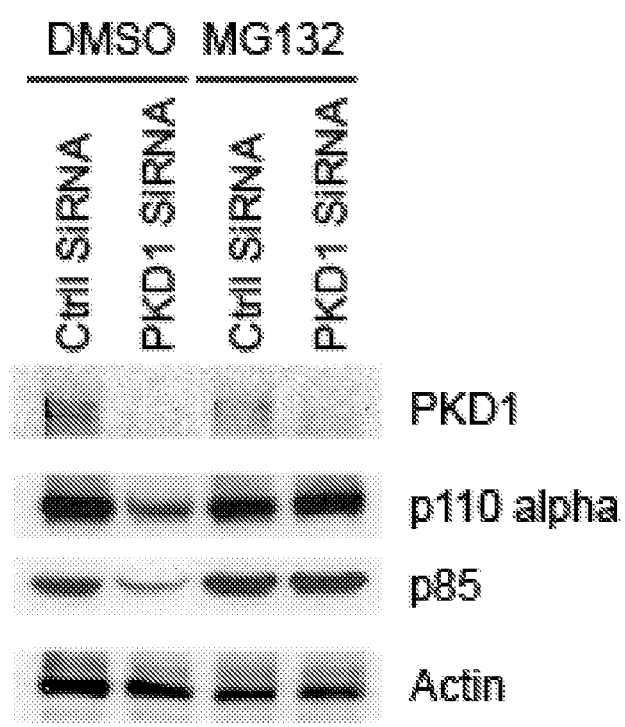
FIG. 5. A proteasome inhibitor, MG132, reversed the level of p110 alpha and p85.

In another experiment, a triple negative breast cancer cell line (HS578T), an ER positive cell line (MCF7) and an ER, Her2 positive cell line (BT474) were transfected with control siRNA or PKD1 specific RNA to down regulate endogenous PKD1 levels. Control or PKD1 downregulated cells were then treated with paclitaxel or control (no treatment) to determine the effect of PKD1 on taxane sensitivity (FIG. 3). These results demonstrated that knockdown of PKD1 sensitized the cells to paclitaxel as assessed by reduced cell survival. Markedly reduced levels of PI3K p110α and p85 subunits as well as PI3K downstream phosphorylated AKT levels (p308AKT and p473AKT) were observed with the PKD1 knockdown cells (FIG. 4). The administration of MG-132, a proteosome inhibitor, reversed this effect, suggesting that PKD1 is targeted for degradation through the proteosome mediated pathway (FIG. 5).

Figure 6A:
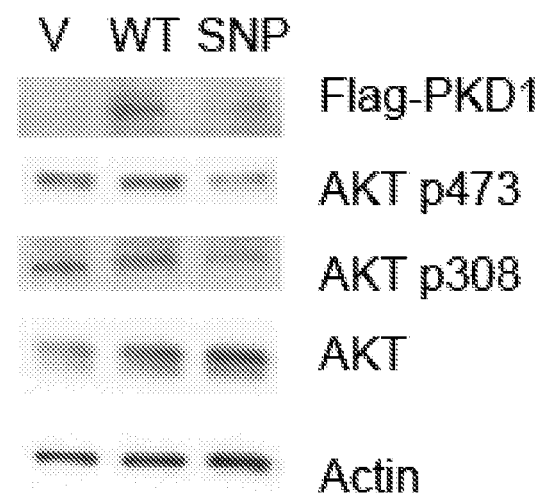
FIG. 6A. MCF7 breast cancer cells were transfected with vector (V), Flag-wild type PKD1 (W) and Flag-SNP PKD1 (V). Twenty-four hours later, cells were harvested, and a Western blot was performed with the indicated antibodies.
Figure 6B:
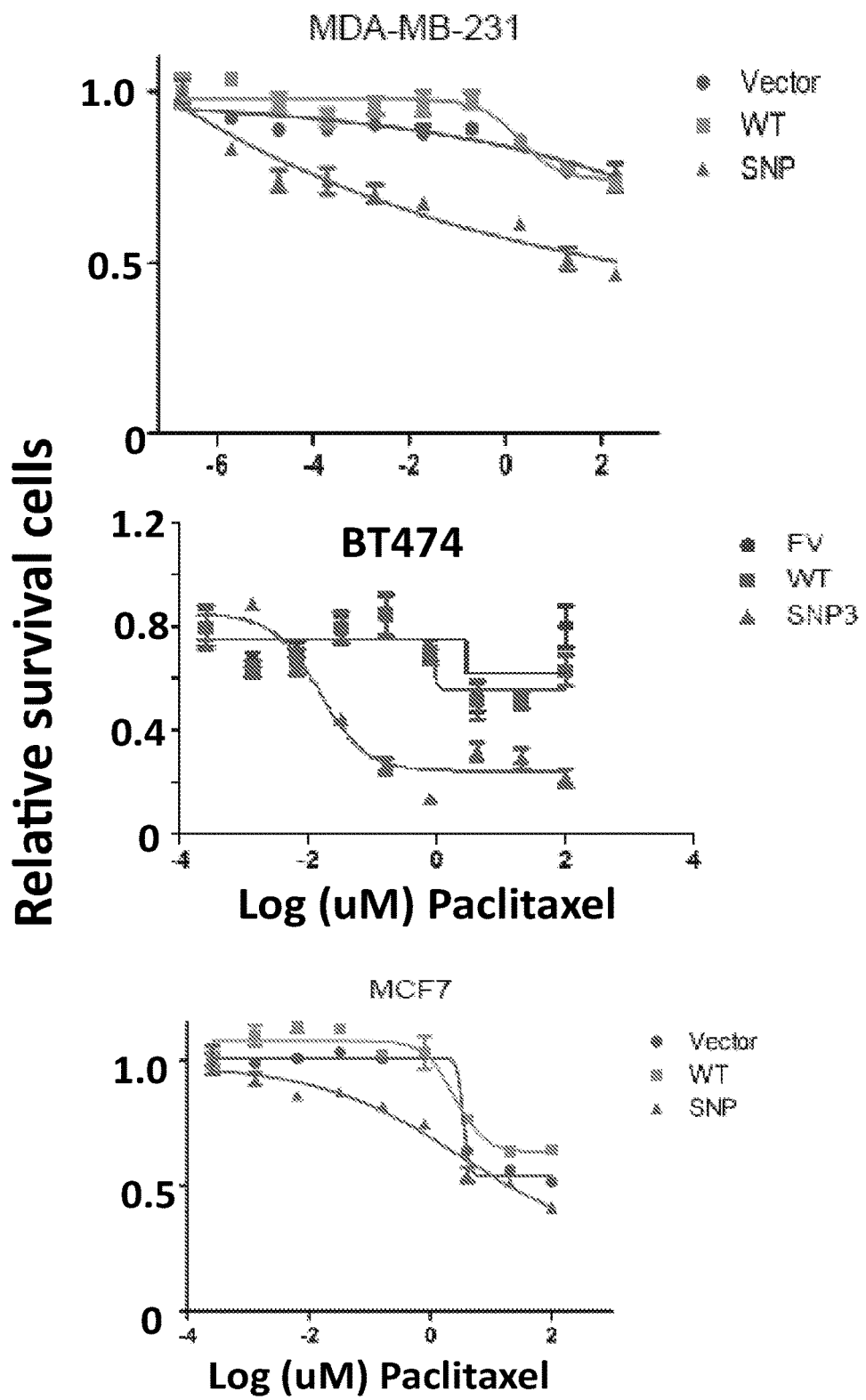
FIG. 6B. SNV rs148709380 sensitizes breast cancer cells to taxane treatment. WT or Variant PKD1 was overexpressed in indicated breast cancer cells, followed by cytotoxicity assays.

To further assess the effects of the variant of the PKD1 gene (PKD1 Chr.16_2164211_G_A; A allele of rs148709380) on response to paclitaxel, breast cancer lines were screened for the variant. Breast cells were overexpressed WT and the PKD1 construct containing the SNPs and protein levels, and response to paclitaxel was tested. It showed that the SNP resulted in reduced PKD1 protein levels and downstream PI3K signaling (FIG. 6A). Additionally, compared with WT, cells transfected with the variant PKD1 construct was more sensitive to taxane treatment (FIG. 6B).

These results demonstrate that PKD1 levels are associated with tumor response in women with breast cancer treated with paclitaxel. In addition, a PKD1 variant (PKD1 16_2164211_G_A; G→A allele of rs148709380) was identified and found to be associated with paclitaxel response.

Figure 7:
FIG. 7. Downregulation of USP2 using specific shRNA destabilized P110α and p85 and downstream AKT activity (pAKT308 and 473).
Figure 8:
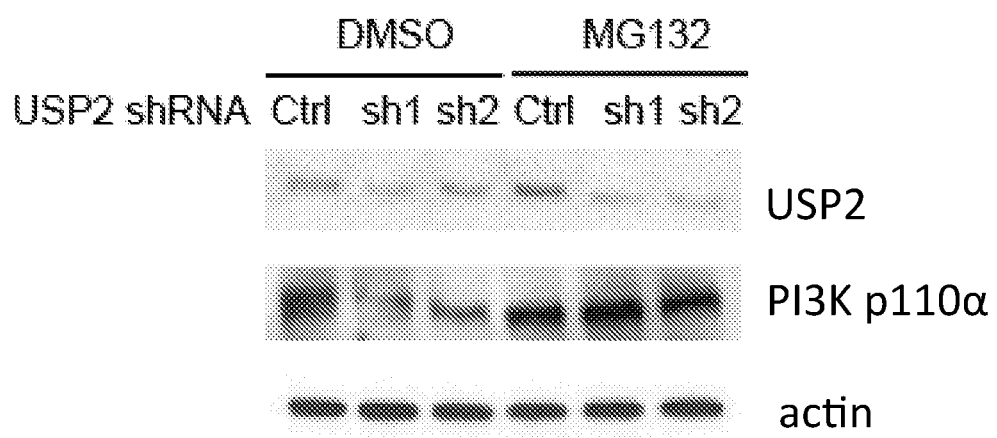
FIG. 8. AU565 cells were infected with control shRNA and two USP2 shRNA, 1 and 2. After 48 hours selection with puromycin, cells were replated. Cells were treated with DMSO or MG132 for 4 hours.
Figure 9:
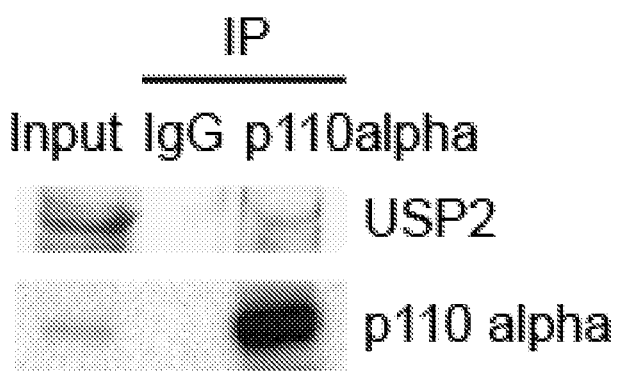
FIG. 9. USP2 interacts with PI3K p110 alpha subunit.
Figure 10A:
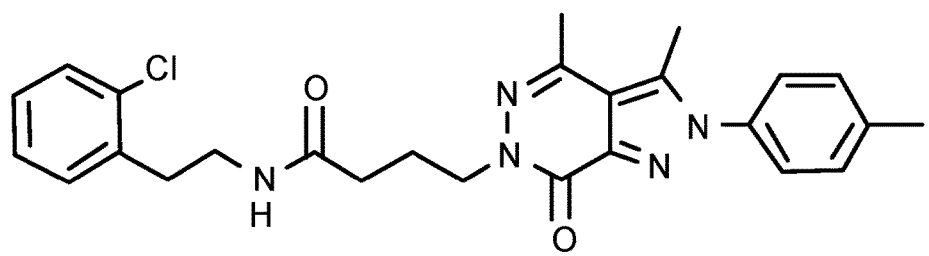
FIGS. 10A-G. Chemical structures of exemplary USP2 inhibitors.
Figure 10B:
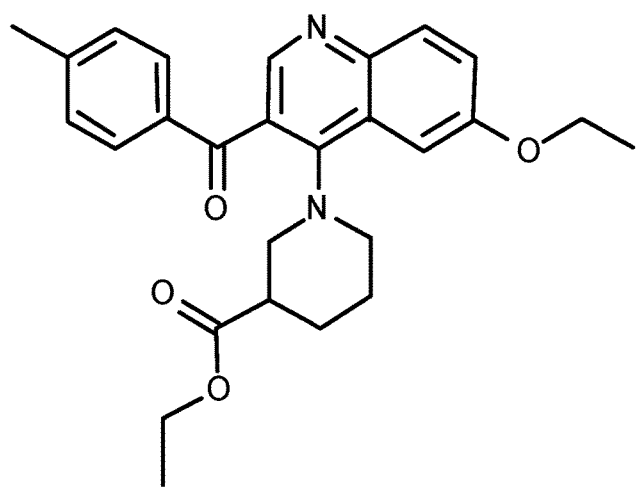
Figure 10C:
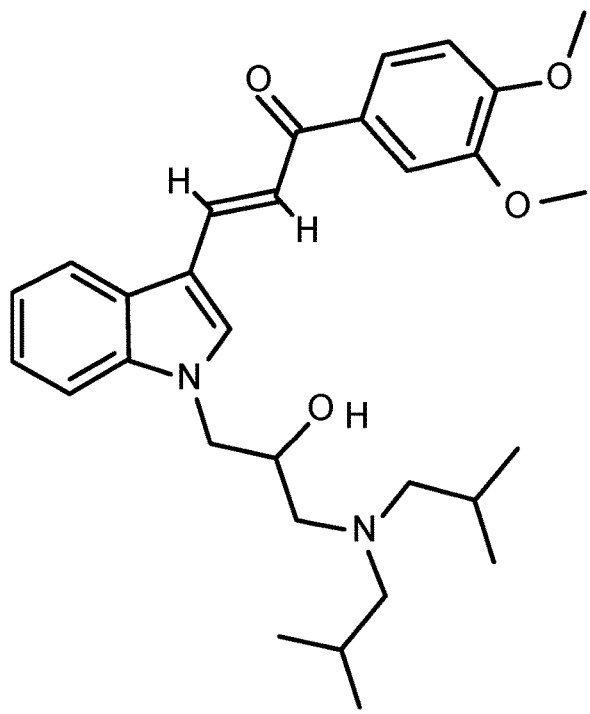
Figure 10D:
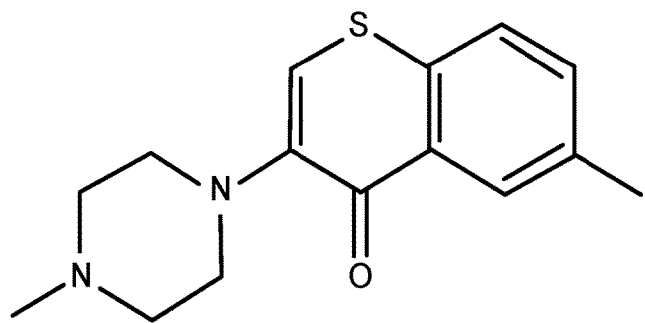
Figure 10E:
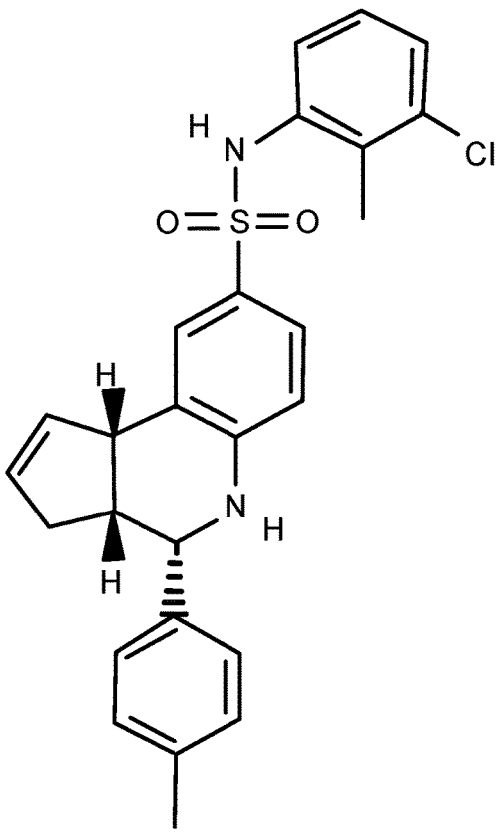
Figure 10F:
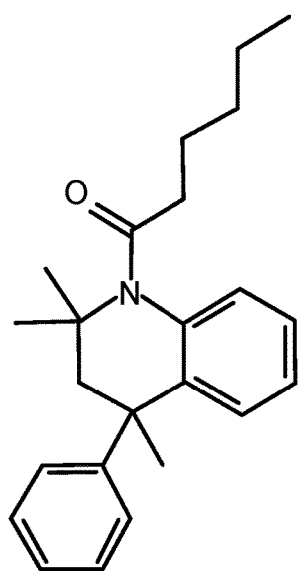
Figure 10G:
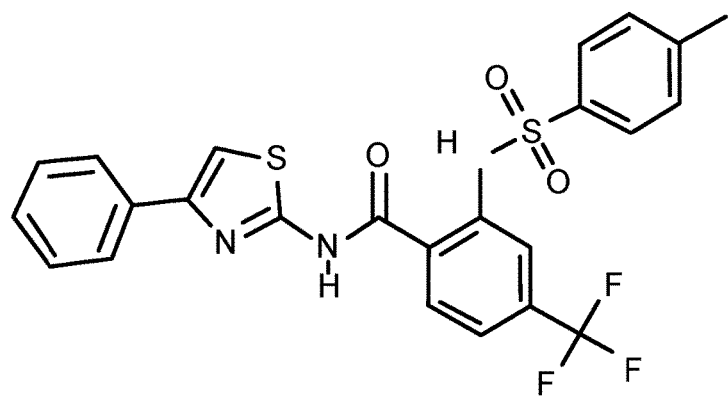

In another experiment, PKD1 was found to influence PI3K-AKT activity by regulating the stability of PI3K p110 alpha subunit through USP2. Down regulation of USP2 destabilized PI3K p110α subunit through increased proteasome mediated degradation process. Briefly, specific siRNA for USP2 were transfected into breast cancer cells and PI3K p110α subunit, and downstream signaling proteins were determined through Western blot analysis using antibody specific for each of the protein (FIG. 7). When the cells treated with a proteasome inhibitor, MG132, the level of PI3K p110α subunit reversed (FIG. 8). Finally, USP2 interacts with PI3K p110α subunit (FIG. 9). The phenotype of PKD1 variant was very similar to that of PKD1 down regulation, in which the variant causes PI3K destabilization. These results suggest that the variant influences response to chemotherapy by down regulating PI3K and in turn, decreasing the proliferation rate.

These results demonstrate that USP2, a deubiquitin enzyme, provides the link between PKD1 and PI3K p110α subunit that helps regulate the stability of PI3K. These results also demonstrate that USP2 inhibitors can be used to sensitize breast cancer cells to several different chemotherapies including taxanes, presumably by destabilizing PI3K and inactivating the PI3K pathway (FIG. 1).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for treating breast cancer, wherein said method comprises:
(a) administering an inhibitor to a mammal having breast cancer and a GA allele of rs148709380, wherein said inhibitor is selected from the group consisting of

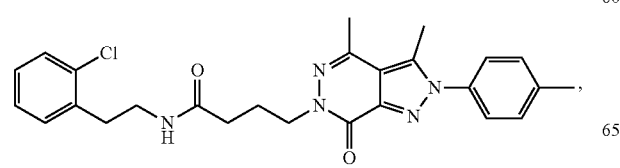

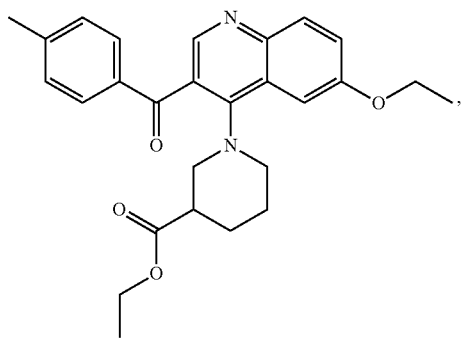

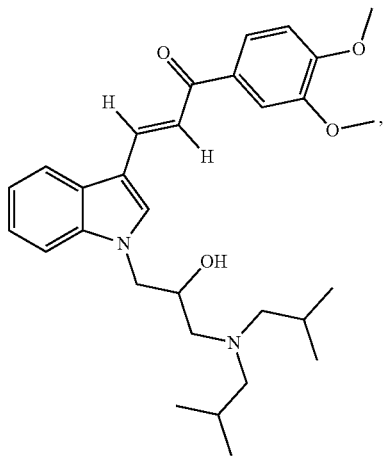

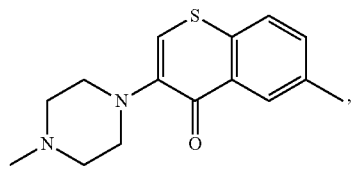

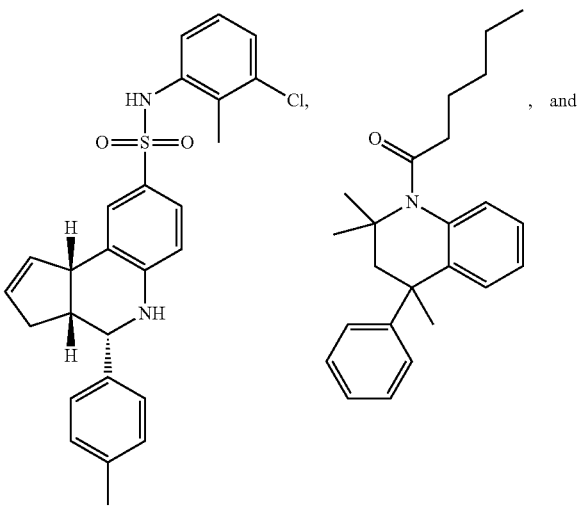

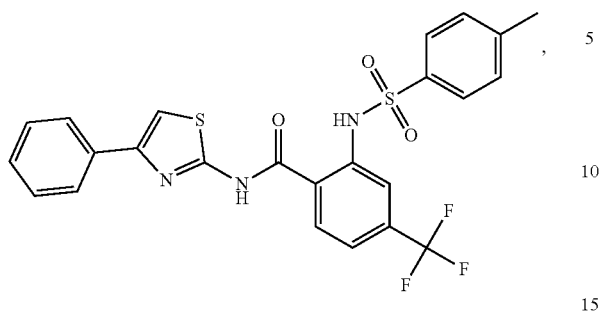

and (b) administering a chemotherapeutic agent to said mammal.

2. The method of claim 1, wherein said mammal is a human.

3. The method of claim 1, wherein said chemotherapeutic agent is a taxane agent.

4. The method of claim 1, wherein said inhibitor is

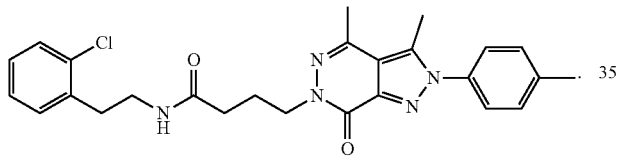

5. The method of claim 1, wherein said inhibitor is

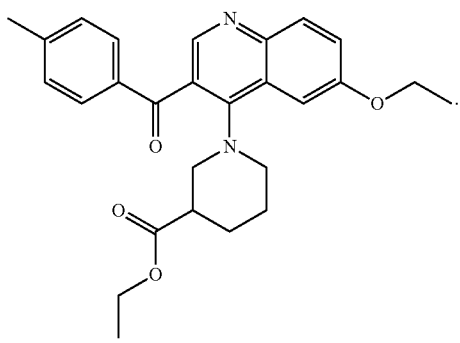 [SMILES: CCOC(=O)C1CCCN(c2c(C(=O)c3ccc(C)cc3)cnc3ccc(OCC)cc23)C1]

6. The method of claim 1, wherein said inhibitor is

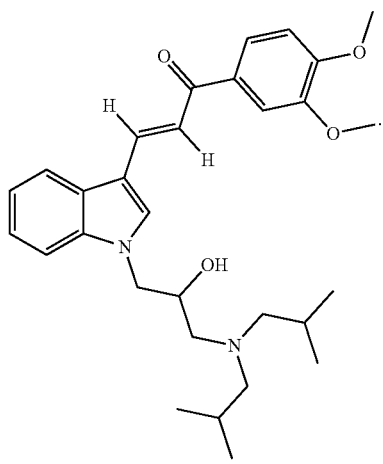 [SMILES: COc1ccc(C(=O)/C=C/c2cn(CC(O)CN(CC(C)C)CC(C)C)c3ccccc23)cc1OC]

7. The method of claim 1, wherein said inhibitor is

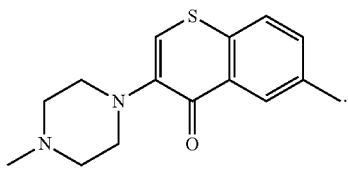

8. The method of claim 1, wherein said inhibitor is

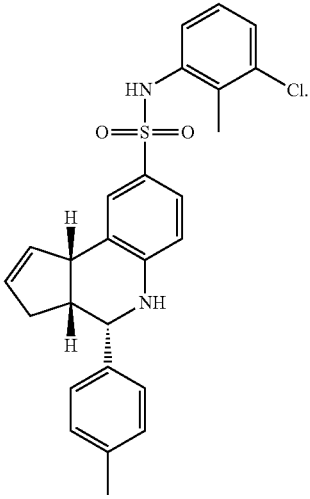 [SMILES: Cc1ccc([C@H]2Nc3ccc(S(=O)(=O)Nc4cccc(Cl)c4C)cc3[C@H]3C=CC[C@H]32)cc1]

9. The method of claim 1, wherein said inhibitor is
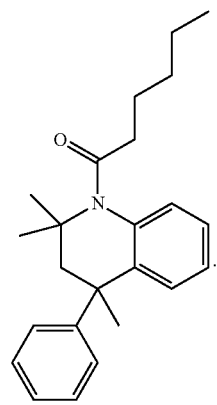 [SMILES: CCCCCC(=O)N1c2ccccc2C(C)(c2ccccc2)CC1(C)C]
10. The method of claim 1, wherein said inhibitor is
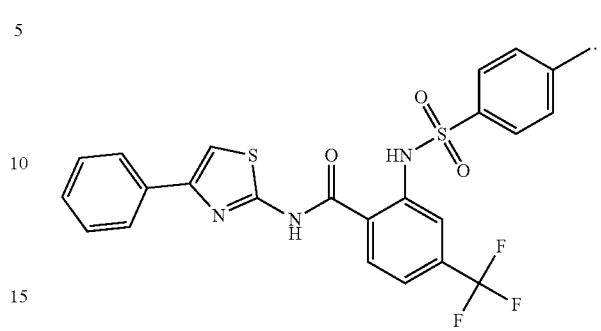
* * * * *

UNITED STATES PATENT AND TRADEMARK OFFICE
CERTIFICATE OF CORRECTION

PATENT NO. : 10,220,016 B2
APPLICATION NO. : 15/551123
DATED : March 5, 2019
INVENTOR(S) : Matthew P. Goetz et al.

Page 1 of 1

It is certified that error appears in the above-identified patent and that said Letters Patent is hereby corrected as shown below:

In the Specification

Column 1, Line 14, please delete "application is applications are" and insert -- applications are --, therefor.

In the Claims

Column 9, Line 57 (Claim 1), please delete "GA" and insert -- G→A --, therefor.

Signed and Sealed this
Thirtieth Day of June, 2020

Andrei Iancu
*Director of the United States Patent and Trademark Office*